United States Patent [19]

Torres

[11] Patent Number: 5,033,128
[45] Date of Patent: Jul. 23, 1991

[54] GOGGLES

[76] Inventor: Telesford E. A. Torres, 5320 Derry, Apt, I (i), Agoura Hills, Calif. 91301

[21] Appl. No.: 461,840

[22] Filed: Jan. 8, 1990

[51] Int. Cl.⁵ .......................... A61F 9/02; A62B 7/02
[52] U.S. Cl. ........................................ 2/427; 2/439; 128/205.22
[58] Field of Search .................. 2/436, 437, 440, 428, 2/430, 9, 439, 427, 431, 442; 128/201.15, 204.18, 205.22, 205.25; 351/43, 44

[56] References Cited

U.S. PATENT DOCUMENTS

| | | | |
|---|---|---|---|
| 2,387,522 | 10/1945 | Maurer | 128/201.15 |
| 2,435,653 | 2/1948 | Maurer | 128/201.15 |
| 2,642,574 | 6/1953 | Eloranta | 2/427 |
| 2,897,817 | 8/1959 | Marina | 128/205.25 X |
| 4,571,748 | 2/1986 | Carroll et al. | 2/439 X |
| 4,951,322 | 8/1990 | Lin | 2/439 |

Primary Examiner—Peter Nerbun
Attorney, Agent, or Firm—Jack C. Munro

[57] ABSTRACT

A goggles through which air is to be breathed by the user. During the breathing of the air, the air is filtered through the side walls of the goggles. There may also be incorporated an oxygen supply tube in conjunction with the goggles to increase the oxygen intake of the user over that of ambient air.

1 Claim, 1 Drawing Sheet

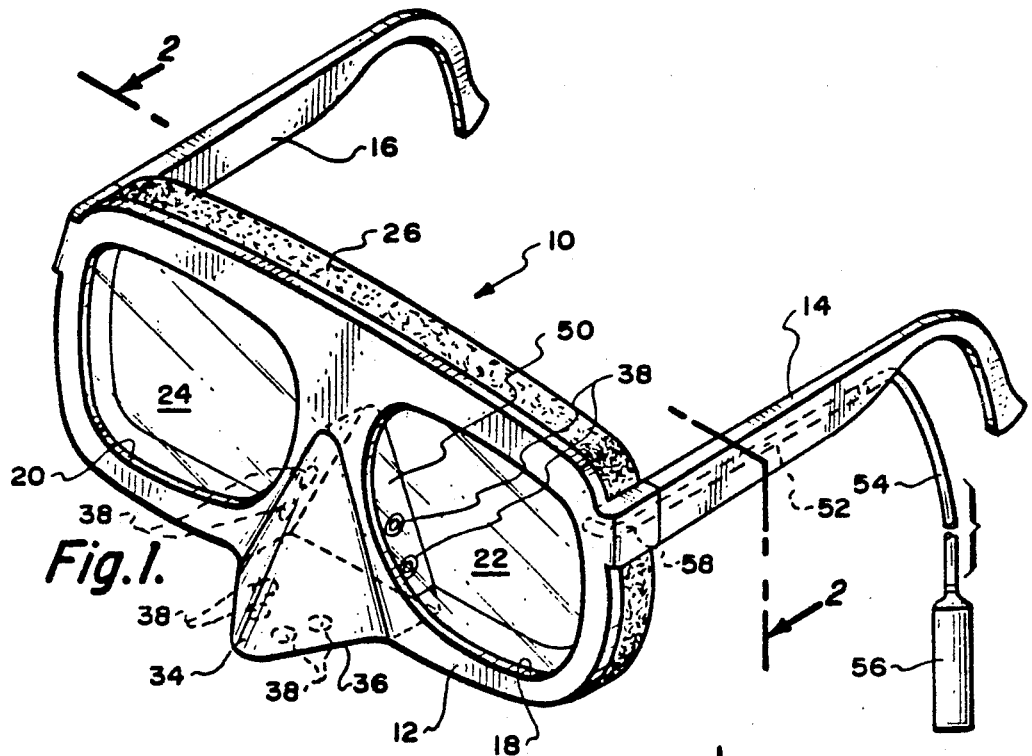
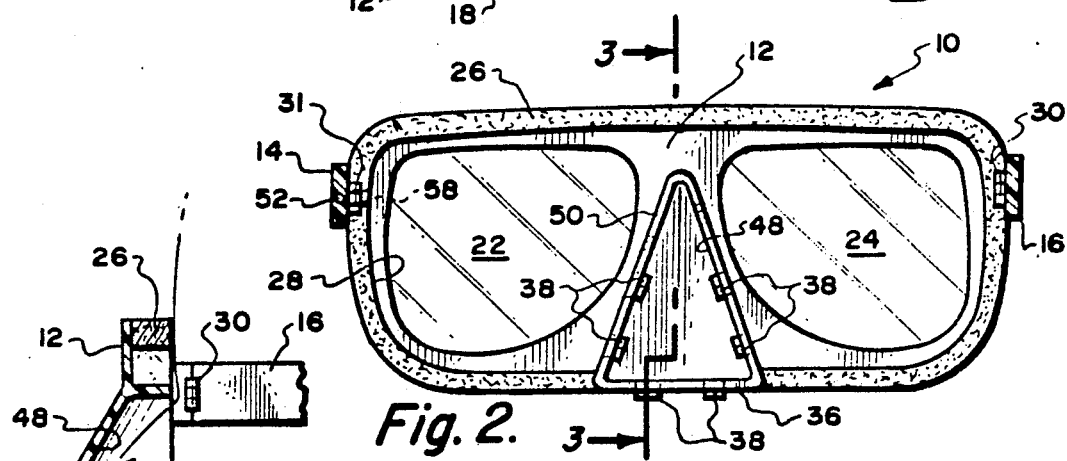
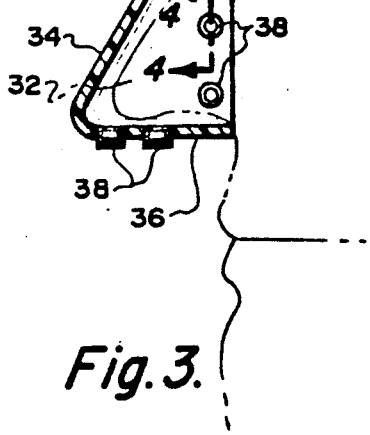
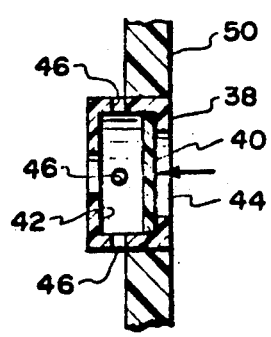
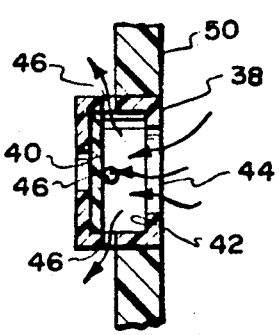

GOGGLES

BACKGROUND OF THE INVENTION

The field of this invention relates to eye wear for human beings and more particularly to a goggles which when worn supplies substantially clean, as well as oxygen increased, air to the nose of the human being wearer of the goggles.

The goggles of the present invention are primarily intended to be used in conjunction with outdoor sports such as skiing, snow mobiling, and other similar activities. However, it is considered to be within the scope of this invention that the goggles could be used in conjuction with any rigorous activity whether indoors or outdoors. It is also considered to be within the scope of this invention that the goggles could be utilized in conjunction with a work activity as opposed to a recreational activity.

Contamination of the air by particulate matter is an exceedingly common problem. Many times outdoor recreational activities are to be performed in environments where the air contains increased levels of particulate matter. During the performing of the activity, the human being has increased breathing and therefore is breathing in increased levels of particulate matter. Breathing in normal levels of the particulate matter is undesirable let alone breathing in increased levels. Also, the breathing in of increased levels hinders the performing of the physical activity.

It is also well-known that when performing a rigorous activity that if the individual performing that activity is supplied of a small amount of oxygen, the individual is capable of recovering more quickly from the physical activity. That individual is also capable off performing at that activity for longer periods of time.

SUMMARY OF THE INVENTION

The structue of the present invention relates to goggles which are designed to tightly fit to the face of the wearer. Surrounding the eye are of the wearer is an enclosed chamber with there being a seperate nose receiving chamber through which the user is to intake air into his lungs and exhale into the ambient. Associated with the peripheral edge of the goggles is a filter strip. Ambient air must be drawn through this filter strip into the enclosed chamber and then through a one-way valve assembly into the nose receiving chamber. Associated with a temple member of the goggles, there is a gas conduit which connects with the enclosed chamber. Through this gas conduit may be supplied a small amount of pure oxygen from a portable pressurized container which contains oxygen so that, as the human being breathes, increased levels of oxygen is inhaled than what is obtainable from the ambient.

The primary objective of the present invention is to construct a goggle which not only functions as safety eye wear and provide protection from ultra-violet light, but also causes the wearer to breathe cleaner air than what is available within ambient air.

Another objective of the present invention is to construct a goggles that is connected both to a source of pressurized oxygen which will permit the oxygen to be supplied into the goggles so that the individual will breathe an increased level of oxygen during the time the goggles are being worn.

Another objective of the present invention is to construct a goggles in a simple manner which is therefore inexpensive to manufacture and therefore can be sold to the consumer at a reasonable price.

BRIEF DESCRIPTION OF THE DRAWING

FIG. 1 is an isometric view of the goggles of the present invention;

FIG. 2 is a back view of the goggles of the this invention, partly in cross-section, taken along line 2—2 of FIG. 1;

FIG. 3 is a cross-sectional view through the nose receiving chamber incorporated within the goggles of the present invention taken along line 3—3 of FIG. 2;

FIG. 4 is a cross-sectional view through one of the one-way valves utilized in conjunction with the nose receiving chamber of the goggles of the present invention taken along line 4—4 of FIG. 3 showing the valve in the closed position; and FIG. 5 is a view similar to FIG. 4 but showing the one-way valve in the open position.

DETAILED DESCRIPTION OF THE SHOWN EMBODIMENT

Referring particularly to the drawing, there is shown the goggles 10 of this invention which is composed of lens frame 12, a left temple member 14 and a right temple member 16. Formed within the lens frame 12 are a pair of enlarged openings 18 and 20. The openings 18 and 20 are adapted to be located directly adjacent the eyes of a human being wearer. Opening 18 is to be located directly adjacent the left eye of the wearer and opening 20 is to be located directly adjacent the right eye. Within opening 18 is to be mounted a transparent lens 22. A similar lens 24 is to be located within the opening 20. Normally, the frame 12 as well as the temple members 14 and 16 will be constructed of a plastic. However, any sufficiently rigid material will suffice.

The temple members 14 and 16 are each independently pivotally connected to the lens frame 12. Constructing of eye wear using a lens frame such as lens frame 12 and temple members, such as temple members 14 and 16, is deemed to be conventional. The temple members 14 and 16 are pivotally connected to the lens frame 12 by a conventional pin-type of pivot joint such as shown as pivot joint 30 for temple member 16 and pivot joint 31 for temple member 14.

The lens frame 12 includes on its interior surface a filter strip 26. This filter strip will normally comprise a fibrous or some type of cellulose material. The filter strip 26 will permit passage of air therethrough but will function to capture particulate matter. The strip 26 will be soft so that it can come into direct contact with the skin of the wearer of the goggles 10 and this contact will be comfortable to the wearer. Normally, the strip 26 will assume a configuration to conform to the face of the human being. This particular configuration is not shown in the drawing. When the strip 26 is in contact with the face of the human being (not shown) there will be formed an enclosed compartment 28 defined by a portion of the lens frame 12, the inside surface of the lenses 20 and 22 and bordered by the face of the wearer. When the wearer inhales air, it is to be only air that has been conducted through the strip 26 and into the enclosed compartment 28.

The nose 32 is totally confined within an inner wall 50 and outer wall 34. The bottom portion 36 of the wall 34 connects directly to the ambient. Inner wall 50 connects only with enclosed chamber 28. Within this bottom portion 36 is located a plurality of valves 38. Each valve 38 is identical and includes a movable disc 40 mounted within a chamber 42. An inlet opening 44 is provided into the chamber 42. A plurality of holes 46 are provided through the side wall of the valve 38.

When the wearer exhales from the nose 32, air is pushed through inlet opening 44 and applied against the disc 40. This causes the disc 40 to move from the position shown in FIG. 4 to the position as shown in FIG. 5. Therefore, the holes 46 are now exposed which then permits the exhaled air to be conducted directly into the ambient.

The wall 34 does not include any valves but forms the exterior wall surface for the nose compartment 48. Formed within the inner wall 50 are a plurality of the valves 38. However, the valves 38 are reversed in position (in other words, turned one hundred eighty degrees) so that the valves 38 in wall 50 are open, as shown in FIG. 5, when the wearer is inhaling. When inhaling, the valves 38 mounted within wall 36 are closed. Now when the wearer exhales, the valves 38 within wall 36 open and the valves 38 mounted within the wall 50 are closed.

Included within temple member 14 is a conduit 52. This conduit 52 is to be connectable through a hose 54 to a pressurized bottle 56. The pressurized bottle 56 is to include oxygen. The oxygen is to be conducted through a very slow leak type of valve arrangement (not shown) that would probably be mounted at the outlet of the pressurized container 56, through the conduit 52, through a conduit 58 mounted within the lens frame 12 to be discharged into enclosed chamber 28. It is the function of the container 56 to increase the level of oxygen within the enclosed chamber 28 that will be inhaled by the wearer.

What is claim is:

1. A goggles comprising:
   a lens frame adapted to be worn on the face of a human being, said lens frame having a peripheral edge, a nose receiving chamber included within said lens frame;
   a pair of transparent lenses mounted within said lens frame, each of said lenses to be located directly adjacent an eye of the human being; and
   a fibrous filter strip mounted on said lens frame at said peripheral edge, said fibrous filter strip permitting passage of air therethrough, said fibrous filter strip physically conforming in a tight manner with the face of the human being so that air from the ambient is to be drawn through said filter strip into said nose receiving chamber;
   an enclosed chamber is formed between said nose receiving chamber and said fibrous filter strip, said lenses connecting with said enclosed chamber; and
   a pair of temple members is attached to said lens frame, said temple members adapted to connect with the ear of the human being to facilitate attaching of said goggles onto the head of the human being, one of said temple members including a gas supply conduit, said gas supply conduit connecting with said enclosed chamber, said gas supply conduit being adapted to connect with a container of pressurized gas the gas of which may be supplied into said enclosed chamber.

* * * * *